United States Patent [19]

Sandel et al.

[11] Patent Number: 5,024,326
[45] Date of Patent: Jun. 18, 1991

[54] MEDICAL INSTRUMENT HOLDER AND SHARPS DISPOSAL CONTAINER

[75] Inventors: Dan Sandel, Tarzana, Calif.; Robert T. Horan, Tucson, Ariz.; Rodolfo Gaba; Bruno J. Ramirez, both of Simi Valley, Calif.

[73] Assignee: Devon Industries, Inc., Chatsworth, Calif.

[21] Appl. No.: 356,131

[22] Filed: May 24, 1989

[51] Int. Cl.⁵ ............................................. B65D 83/10
[52] U.S. Cl. ........................... 206/366; 206/363; 206/364; 206/370; 206/365
[58] Field of Search ............ 206/350, 363, 365, 366, 206/370, 380, 382, 438, 570, 571, 364, 564, 828; 220/1 T

[56] References Cited

U.S. PATENT DOCUMENTS

| | | | |
|---|---|---|---|
| 1,625,035 | 4/1927 | Lilly | 206/365 |
| 2,659,485 | 11/1953 | Duley et al. | 206/365 |
| 3,133,635 | 5/1964 | Gordon et al. | 206/366 |
| 3,331,449 | 7/1967 | Jost | 206/380 |
| 3,380,573 | 4/1968 | Gulotta | 206/370 |
| 3,723,061 | 3/1973 | Stahl | 206/370 |
| 3,727,658 | 4/1973 | Eldridge, Jr. | 206/370 |
| 3,727,749 | 4/1973 | Martin | 206/366 |
| 3,944,069 | 3/1976 | Eldridge, Jr. | 206/365 |
| 4,008,802 | 2/1977 | Freitag | 206/382 |
| 4,013,109 | 3/1977 | Sandel | 206/350 |
| 4,106,620 | 8/1978 | Brimmer et al. | 206/363 |
| 4,151,913 | 5/1979 | Freitag | 206/382 |
| 4,167,230 | 9/1979 | Barratt | 206/382 |
| 4,193,496 | 3/1980 | Barratt | 206/382 |
| 4,243,140 | 1/1981 | Thrun | 206/380 |
| 4,373,629 | 2/1983 | Win et al. | 206/370 |
| 4,418,821 | 12/1983 | Sandel | 206/370 |
| 4,596,329 | 6/1986 | Eldridge, Jr. | 206/382 |
| 4,736,844 | 4/1988 | Scott et al. | 206/370 |
| 4,753,345 | 6/1988 | Goodsir et al. | 206/366 |
| 4,767,008 | 8/1988 | Warnecke et al. | 206/366 |
| 4,936,499 | 6/1990 | Conard et al. | 206/366 |

*Primary Examiner*—David T. Fidei
*Attorney, Agent, or Firm*—Poms, Smith, Lande & Rose

[57] ABSTRACT

A medical instrument holder and sharps disposal device is disclosed wherein a pair of plastic container body halves are provided to be manipulated between opened and closed positions by associated hinge means and a mechanical lock. A medical instrument rest in the form of a one piece molded plastic insert is provided on one of the body halves for positioning medical instruments thereon when the container is in its open position. A cushion of reticulated foam material is provided to receive and envelope the tips of sharps associated with the instruments laid upon the rest. Sharps removal means are provided for assisting in the release of medical instrument sharps from the associated medical instruments. A magnetic means is also provided within one of the container body halves for receiving and holding such removed sharps to facilitate the counting a subsequent disposal thereof within the container when a medical operation has been completed and the sharps and container are to be discarded.

5 Claims, 2 Drawing Sheets

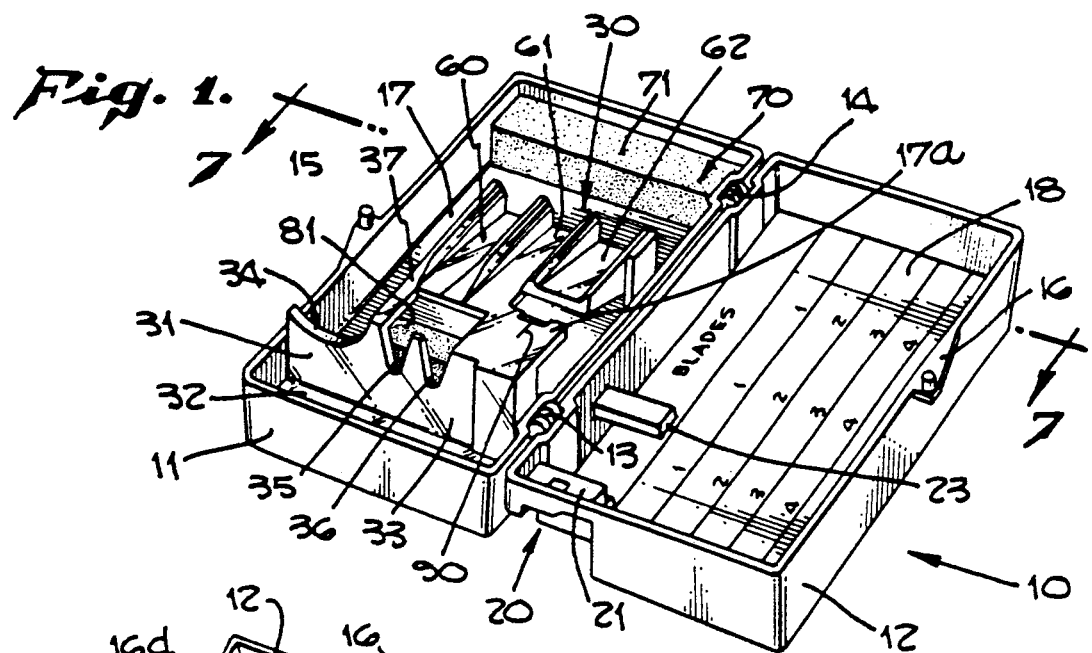
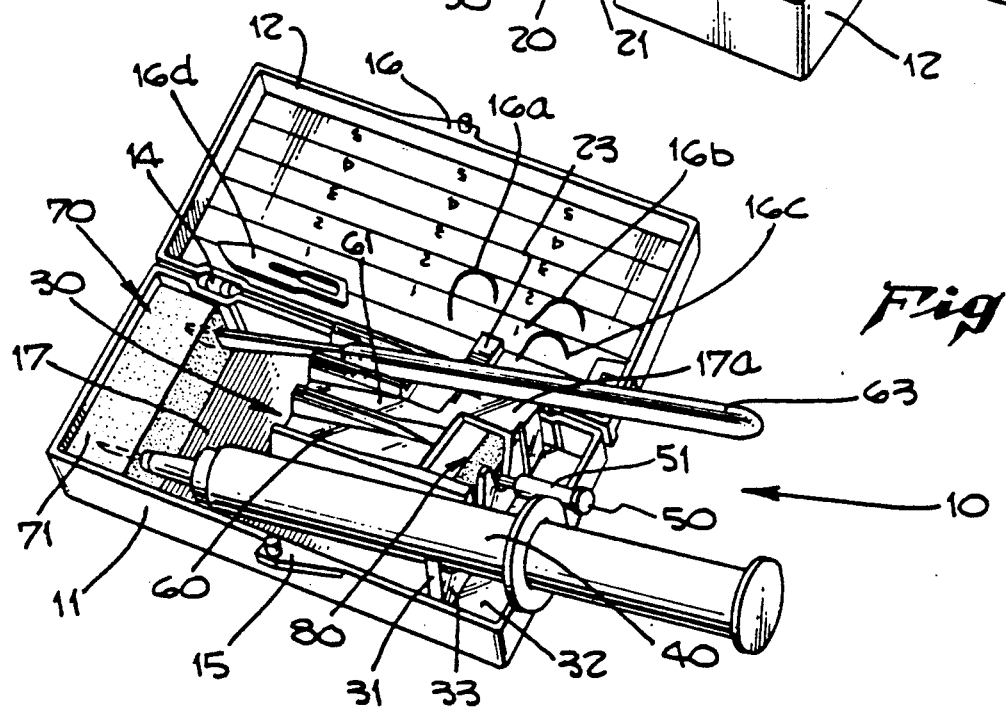
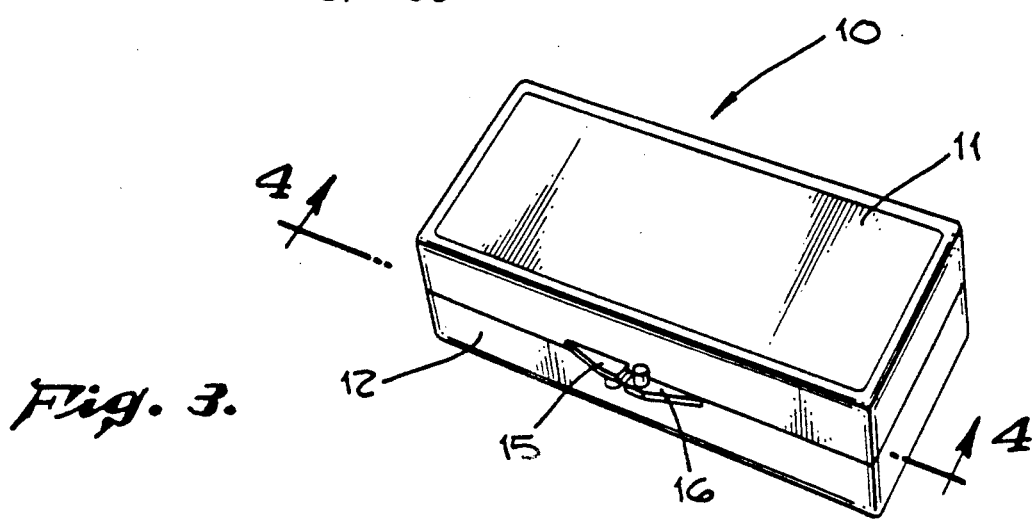

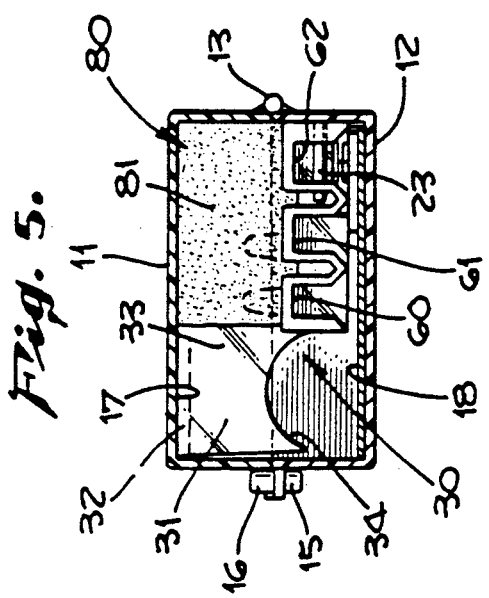
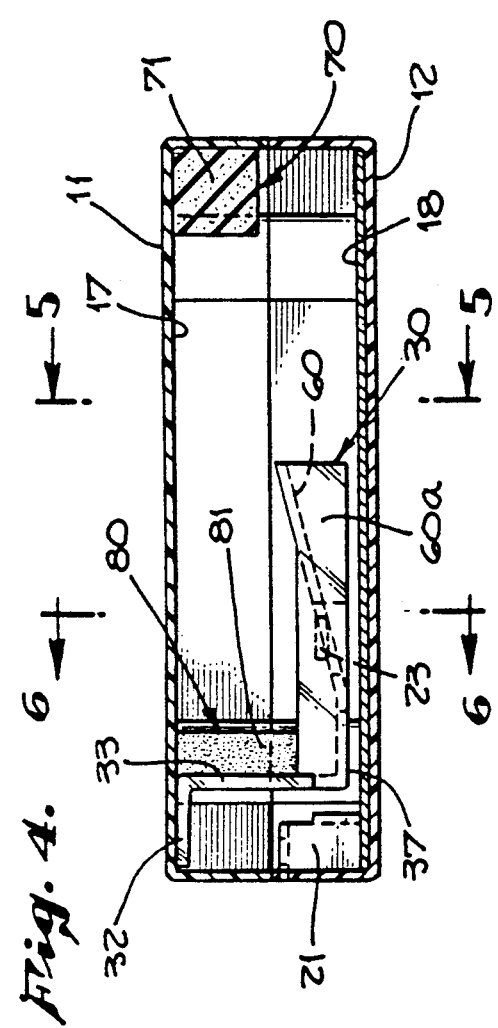
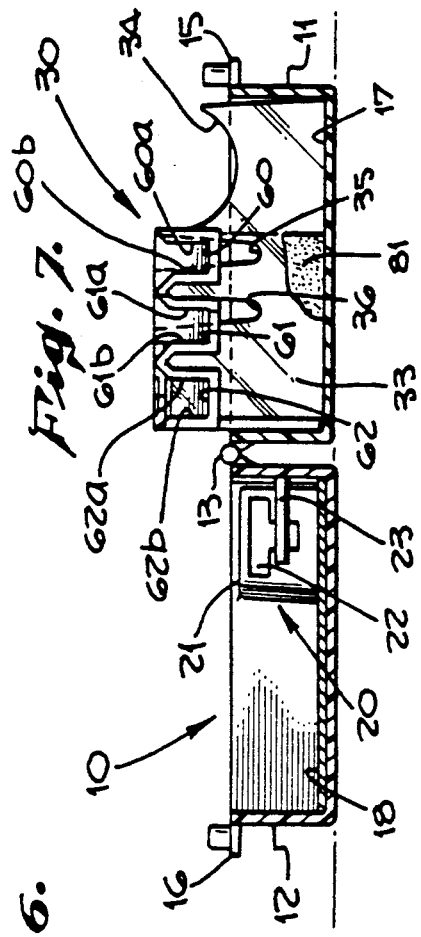
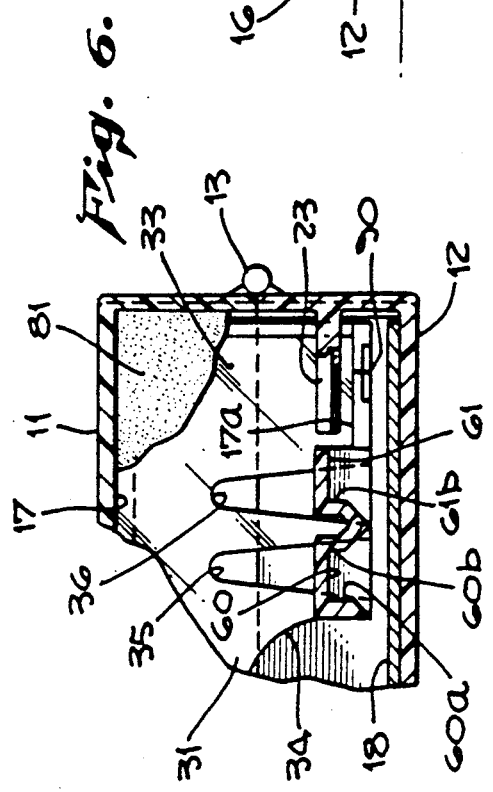

MEDICAL INSTRUMENT HOLDER AND SHARPS DISPOSAL CONTAINER

BACKGROUND OF THE INVENTION.

The present invention relates in general to medical instrument sharps containing and disposal devices and more particularly to such a device which is adapted to facilitate the positioning of medical instruments thereon during medical operations before removal and disposal of the sharps associated with such instruments.

It is common practice during surgical operations for the surgeon to request a syringe with a certain volume of medication for use during the course of the operation, portions only of such medication being injected at any one time. During the intervals between injections, there is a need for a device for positioning the syringe in a sterile safe environment. Presently such syringes and surgical scalpels are commonly simply laid upon a sterile table top when not being used. These items can be accidentally bumped, jostled or otherwise allowed to roll off of such sterile table top in such a manner that not only must such instruments be replaced in a sterile manner, but they may become a hazard to the health of the surgeons and assisting nurses if any one of them is scratched, or receives a skin puncture, by the needle point, blade point or other pointed end of a sharp surgical instrument. This is particularly dangerous to the medical staff where the patient has a communicable disease.

It has thus been recognized that there is a need for a way of handling such syringes, scalpels and related surgical instruments during and after a surgical operation in such a way that medical hazards are not presented to the operating room staff. It would thus be desirable to have a disposable container for disposal and storage of such sharps which could also be employed during and after an operating room operation for positioning and holding such syringes or scalpels in a sterile and secured stationary manner so that the operating room staff, whether it be the operating doctor or surgery room nurse can easily manipulate the sterile instrument for repeated, intermittent use with the instrument being maintained in a safe, non-hazardous and sterile condition during the intervals between such uses.

SUMMARY OF THE INVENTION

In View of the foregoing, it is the primary object of the present invention to disclose and provide a sharps containing and disposal device suitable for providing a medical instrument positioning and retention means thereon with further provision of means for protecting the user of such device from inadvertent punctures or scratches from the tips of the sharps associated with such medical instruments. Preferably, such a device can be itself sterilized and positioned on the available sterile table tops in the operating room for positioning of instruments thereon, facilitate the removal of the sharps from such instruments and then accommodate the safe disposal of the such sharps once the operation is completed.

Generally stated, the present invention in a sharps containing and disposal device intended to accomplish the aforestated objects includes the provision of a medical instrument rest provided within a sterilizable container with a sharps enveloping means also associated with the container whereby a medical instrument may be rested upon the instrument rest with the tip of its associated sharp penetrating and being enveloped by the associated sharps tip enveloping means.

More specifically, the present invention includes the provision of a sharps containing and disposal device as aforestated wherein the medical instrument rest is provided in the form of a sterilizable plastic material insert suitable for adhesive, foam, magnet, (or the like) retention within one half of a two part plastic container or box with such insert providing upwardly facing rest surfaces when the container is laid on an operating room sterile table top in its open position. Further, such device includes a magnetic means within the container to facilitate the retention of sharps removed from such medical instruments as well as the provision of blade removal means to facilitate the removal of blades from a medical instrument which has been positioned upon such rest during a medical operation and, the operation having been completed, is to be disposed of within the container.

More specifically, the exemplary medical instrument rest insert provides a plurality of first rest surfaces of generally channel configuration lying above and inclined to an adjacent underlying container surface which is generally positioned horizontally when the container is in its opened position of use. Medical instruments laid on such inclined channel surfaces are thus inclined relative the horizontal to facilitate the user's grasping the upwardly inclined handle ends of scalpels rested thereon. Such rest may also include an upwardly facing arcuate rest surface for receiving a generally cylindrical configured medical instrument laid thereon, such as a cylindrical bodied syringe. Such arcuate rest surface may be of relatively narrow width whereby the syringe body rested thereon tips down toward the underlying container surface with the free end of the syringe positioned in an upwardly and outwardly inclined manner to facilitate the manipulation thereof by a user.

The sharps tip enveloping means of the present invention may comprise a cushion member made of a reticulated foam material which is suitable for being sterilized and may be provided in a block form adhesively secured within the container generally adjacent the rest. A reticulated foam material may be provided with relatively coarse pores to allow the reception of the tips of needles therein without damaging the material. The provision of such pores also facilitates the sterilizing of the cushion where it is desired to reuse the syringe needle where the contents of the syringe are being injected as individual partial injections of the contents of the syringe.

It is believed that a better understanding of the present invention in a sharps containing and disposal device having a medical instrument rest and associated sharps tip enveloping means, in accordance with the present invention, will be afforded to those skilled in the art from a consideration of the following detailed description of a preferred exemplary embodiment thereof. Reference will be made to the appended sheets of drawings which will first be described briefly.

BRIEF DESCRIPTION OF THE DRAWINGS

FIG. 1 is a perspective view of a preferred exemplary embodiment of the sharps containing and disposal device, in accordance with the present invention, for containing and disposing of sharps removed from associated medical instruments, the device being shown in its opened position ready to receive medical instruments thereon.

FIG. 2 is a view of the device of FIG. 1 showing exemplary medical instruments rested thereon with the associated syringe needles and scalpel blades penetrating the exemplary sterilizable cushion member to protect users from accidental punctures by such needles, blades or other sharps associated with the medical instruments.

FIG. 3 is a perspective view of the sharps containing and disposal device of FIGS. 1 and 2 shown in a closed position wherein it is suitable for containing medical instrument sharps for disposal thereof.

FIG. 4 is a section view of the sharps containing and disposal device of FIG. 3 taken therein along the plane IV—IV.

FIG. 5 is a section view to the device of FIG. 4 taken therein along plane V—V.

FIG. 6 is a detail section view of the device of FIG. 4 taken therein along plane VI—VI.

FIG. 7 is a section view through the exemplary embodiment of sharps containing and disposal device of FIG. 1 taken therein along the plane VII—VII.

DETAILED DESCRIPTION OF A PREFERRED EXEMPLARY EMBODIMENT

A detailed description of the preferred exemplary embodiment of sharps containing and disposal device in accordance with the present invention will now be made with reference being made initially to FIGS. 1 through 3. The exemplary device, indicated generally at 10, includes a plastic material molded container provided in container body halves 11 and 12 which are hinged in known manner by hinges 13 and 14 so that the container body halves 11 and 12 may be provided in the opened position of FIGS. 1 and 2, or in the closed position of FIG. 3. A mechanical lock is provided by the integrally molded lock means 15 and 16, also of known construction, which facilitates the closure of the container, as seen in FIG. 3, with the container halves and 12 held in a locked closed position, for disposal of any sharps contained therein.

In the exemplary embodiment, the container body half 12 is provided with a large magnetic surface 18 covering the entire base of body half 12 in a manner as taught in U.S. Pat. No. 4,013,109. Such magnetic surface may be provided by a rubber magnet material as presently known in the industry with counting indicia thereon to facilitate the counting and retention of medical instrument metallic sharps thereon such as the medical sharps 16a-16d as seen in FIG. 2. In order to facilitate the removal of scalpel blades, such as blade 16d, a blade removal means is provided within the container body half 12 as indicated generally at 20. Such blade removal means is preferably made in accordance with the teachings of U.S. Pat. No. 4,318,473. In the exemplary embodiment, such blade removal means includes the 10 integrally molded boss 21 having T-slot 22 through which the scalpel and scalpel blade are positioned with the tip of such blade below the hold down tab 23. As is disclosed more completely in said U.S. Pat. No. 4,318,473, the disclosure of which is incorporated herein by reference, the scalpel blade may be removed by simply depressing the tip of the blade against the magnetic surface 18 beneath the hold down tab 23 with rear portions of the blade springing away from the scalpel handle as the handle goes down into the vertical depending portion of the T-shaped slot 22, the scalpel blade being thereby separated from the blade retaining means on the scalpel handle allowing the handle to be withdrawn from the T-slot 22 while the blade falls into the container half 12. Counting of the blades may be accomplished in association with the indicia provided upon the magnetic material 18 which retains the metal blade securely for counting and disposal purposes.

As is particularly contemplated within the present invention, a medical instrument rest, indicated generally at 30, is provided within the container to be accessible when the container is placed in its open position as seen in FIGS. 1 and 2. The exemplary embodiment of such instrument rest, indicated generally at 30, is provided in the form of a one piece integrally molded plastics material insert 31 which is secured to the base 17 of container body half 11 by adhesive, sonic welding or other known means for securing plastic material parts together. Insert 31 includes a base flange 32 secured to container body half base 17, as seen in FIG. 4, with an upstanding front wall 33 in which rest surfaces 34, 35 and 36 are molded. Rest surface 34 is provided as an upwardly facing arcuate rest surface to receive cylindrical shaped medical instruments, such as syringe 40 as seen in FIG. 2. Rest surfaces 35 and 36 are provided as upwardly facing wedge configured surfaces to receive smaller diameter medical instrument components such as the needle assembly 50, as seen in FIG. 2, which has been separated from a syringe. Such needle assembly includes a body 51 of circular configuration which can be wedged into the wedge surface, as surface 36, to facilitate separation from the syringe, such as the syringe 40.

As is also particularly contemplated within the present invention, the exemplary embodiment of medical instrument rest, indicated generally at 30, is provided with a plurality of channel configuration rest surfaces 60, 61 and 62 which are formed integrally of the insert top flange 37. Each of the channel rest surfaces 60, 61 and 62 are provided in a plane which is inclined toward the container body half base 17, and in particularly such rests are inclined downwardly as the surfaces extend rearwardly of front surface 33. Such inclination of the rest surfaces 60, 61 and 62 facilitates the inclination of medical instruments, such as the scalpel 63, as seen in FIG. 2, which is shown rested on surface 62 such that the free upward end of the scalpel is accessible to an user while the pointed blade end is positioned downwardly adjacent the container half base 17. As seen in FIG. 7, the configuration of the channel rests 60, 61, and 62 are provided by the vertical side walls 60a, 60b, 61a, 61b, 62a, and 62b, respectively, all of such side walls being formed integrally of the one piece plastic material insert 31.

In order to ensure protection of the user of the medical instrument rest, in accordance with the present invention, from inadvertent injuries or punctures by the tips of the sharp medical instrument scalpel blades, needle points, and the like, generally referred to as sharps, a sharps tip enveloping means, indicated generally at 70, is provided within the container body half 11 generally adjacent the rest. Thereby, the tips of sharps associated with medical instruments laid upon the rest, as seen in FIG. 2, may penetrate and be enveloped by such enveloping means to protect the users of the device from inadvertent punctures which might otherwise occur due to mishandling of the medical instruments or the rest device when such instruments are placed thereon. In the exemplary embodiment, such sharps tip enveloping means, indicated generally at 70, includes the provision of a cushion member 71 made of a reticulated sterilizable foam material which has openings or pores therein to facilitate the penetration of the points of the sharps. In the case of needles, the needle points may penetrate the pores of the reticulated foam cushion member 71 without damaging the material.

Such cushion member 71 may be secured within the container body half 11 by the use of adhesive means or other presently known means for securing reticulated foam to a plastic base. An additional sharps tip enveloping means, indicated generally at 80 in FIGS. 2, 4 and 5, is provided directly behind and in engagement with the front wall 33 of insert 31 to be in a position to receive the needle points of needle assemblies positioned upon the wedge shape rests 35 and 36, as seen in FIG. 2. Such additional sharps tip enveloping means may comprise a cushion member 81 in the form of a reticulated foam material block secured to the surface of base 17 and the rear surface of front wall 33 as best seen in FIGS. 4 and 5.

An additional blade removal means is provided in the exemplary embodiment of rest insert 31, such additional blade removal means comprising a slot 90, as seen in FIGS. 1 and 6, provided in the forward, generally horizontal surface portion 17a of top surface 17. When appropriate, the blade of a surgical instrument may be secured in slot 90 as the associated instrument is released from the blade. Such blade can then be positioned on magnetic surface 15 for counting and subsequent disposal.

Having thus described a preferred exemplary embodiment of sharps containing and disposal device having a medical instrument rest as well as the sharps tip enveloping means associated therewith in accordance with the present invention, it should be apparent to those skilled in the art that various medical instruments may be laid upon the rest when the device is in its open position as seen in FIG. 2, with the points of the associated sharps protected by the enveloping action of the cushion members 70 and 80. The needle assemblies of syringes may be removed through the use of the syringe needle removal wedge surfaces 35 and 36. Scalpel blades may be removed through the use of the blade removal slot 90 and/or the blade removal means indicated generally at 20. Such medical instrument sharps may be placed upon and held to the container surface 18 via the magnetic attraction provided by surface 15 so that after counting thereof, the container may be simply closed and discarded along with its contents in a manner which protects medical personnel from the dangers of inadvertent punctures by such medical sharps. It is believed that those skilled in the art will appreciate that the aforestated advantages and objects of the within invention have been attained by the exemplary embodiment thus disclosed and that various additional embodiments, adaptations and modifications thereof may be made within the scope of the present invention which is defined by the following claims.

We claim:

1. A medical instrument holder and sharps disposal device comprising:
   a pair of container body halves having an open position wherein medical instruments and sharps may be positioned thereon and a closed position wherein sharps contained therein may be disposed along with said device;
   a medical instrument rest on one of said halves which presents at least one upwardly facing rest surface for receiving portions of a medical instrument rested thereon;
   sharps removal means for removing sharps from medical instrument bodies which have been rested upon said rest;
   magnetic means within said device for receiving and holding such sharps which have been removed from said instruments for facilitating the counting thereof and subsequent disposal thereof along with said device; and
   a sharps tip receiving and protecting member into which the tips of sharps associated with medical instruments rested upon said rest may penetrate to protect a user thereof from the tips of said instruments while they are rested on said device.

2. The medical instrument holder and sharps disposal device of claim 1 wherein said sharps tip receiving and protecting member comprises:
   a cushion of a sterilizable reticulated foam material capable of enveloping tips of sharps inserted therein without being damaged thereby.

3. A disposable, sterilizable plastic material device for facilitating the positioning of medical instruments having sharps associated therewith such as syringe needles, scalpel blades and the like during use thereof which facilitates the counting of such sharps and the subsequent disposal thereof, said device comprising:
   a first container part having a magnetized material surface with indicia thereon for positioning, retaining and counting sharps laid thereon;
   a second container part having an instrument positioning rest extending above an adjacent surface of said second part to facilitate the positioning of a medical instrument on said second part with a portion at least of said instrument extending upwardly away from said adjacent surface;
   hinge means for hinging said first and second parts together to facilitate their being positioned in a side by side open position for receiving medical instruments thereon; and
   a safety cushion member provided on said second container part and positioned relative said rest so that at least the tip of a sharp associated with a medical instrument positioned on said rest penetrates said member as a protection to any inadvertent puncture of the skin of a person manipulating said instrument and/or device as might otherwise occur if said tip where not so protected.

4. The disposable, sterilizable plastic material device of claim 3 wherein said safety cushion member comprises:
   a reticulated foam material presenting a plurality of opening into which the tips of sharps may be received. penetrates said member as a protection to any inadvertent puncture of the skin of a person manipulating said instrument and/or device as might otherwise occur if said tip where not so protected.

5. The device of claims 1 or 3 further comprising:
   a needle tip receiving cushion positioned below portions of said rest to receive tips of needles placed on said rest.

* * * * *